United States Patent
Fack et al.

(10) Patent No.: US 9,849,071 B2
(45) Date of Patent: Dec. 26, 2017

(54) COMPOSITION FOR THE OXIDATION DYEING OF KERATIN FIBRES, COMPRISING PARTICULAR FATTY ALCOHOLS, A LIQUID FATTY SUBSTANCE AND A CATIONIC POLYMER

(71) Applicant: L'Oreal, Paris (FR)

(72) Inventors: Géraldine Fack, Levallois-Perret (FR); Amine Megueni, Paris (FR); Luc Nicolas-Morgantini, Rully (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/367,042

(22) PCT Filed: Dec. 18, 2012

(86) PCT No.: PCT/EP2012/075915
§ 371 (c)(1),
(2) Date: Jun. 19, 2014

(87) PCT Pub. No.: WO2013/092562
PCT Pub. Date: Jun. 27, 2013

(65) Prior Publication Data
US 2014/0366907 A1 Dec. 18, 2014

Related U.S. Application Data

(60) Provisional application No. 61/593,477, filed on Feb. 1, 2012.

(30) Foreign Application Priority Data

Dec. 19, 2011 (FR) ..................................... 11 61962

(51) Int. Cl.
| | | |
|---|---|---|
| *A61Q 5/10* | (2006.01) | |
| *A61K 8/22* | (2006.01) | |
| *A61K 8/31* | (2006.01) | |
| *A61K 8/34* | (2006.01) | |
| *A61K 8/37* | (2006.01) | |
| *A61K 8/39* | (2006.01) | |
| *A61K 8/41* | (2006.01) | |
| *A61K 8/86* | (2006.01) | |
| *A61K 8/92* | (2006.01) | |
| *A61K 8/81* | (2006.01) | |
| *A61K 8/84* | (2006.01) | |
| *A45D 19/02* | (2006.01) | |
| *A61K 8/36* | (2006.01) | |
| *A61K 8/69* | (2006.01) | |

(Continued)

(52) U.S. Cl.
CPC ................ *A61K 8/22* (2013.01); *A45D 19/02* (2013.01); *A61K 8/31* (2013.01); *A61K 8/34* (2013.01); *A61K 8/342* (2013.01); *A61K 8/36* (2013.01); *A61K 8/37* (2013.01); *A61K 8/39* (2013.01); *A61K 8/41* (2013.01); *A61K 8/69* (2013.01); *A61K 8/817* (2013.01); *A61K 8/8152* (2013.01); *A61K 8/84* (2013.01); *A61K 8/86* (2013.01); *A61K 8/92* (2013.01); *A61K 8/922* (2013.01); *A61Q 5/10* (2013.01); *A45D 2007/001* (2013.01); *A45D 2019/0066* (2013.01); *A61K 2800/10* (2013.01); *A61K 2800/4324* (2013.01); *A61K 2800/882* (2013.01)

(58) Field of Classification Search
CPC ... A61Q 5/10; A61K 8/22; A61K 8/37; A61K 8/39; A61K 8/34; A61K 8/41; A61K 8/86; A61K 8/922; A61K 8/924; A61K 8/8152; A61K 8/817; A61K 2800/882; A61K 2800/4324; A61K 2800/10; A45D 2007/001; A45D 2019/0066
USPC ............................................................. 8/405
See application file for complete search history.

(56) References Cited

U.S. PATENT DOCUMENTS

| 6,238,653 | B1 | 5/2001 | Narasimhan | |
|---|---|---|---|---|
| 2002/0010970 | A1 * | 1/2002 | Cottard et al. | .................... 8/405 |

(Continued)

FOREIGN PATENT DOCUMENTS

| EP | 2 198 927 A2 | 6/2010 |
|---|---|---|
| EP | 2 246 039 A1 | 11/2010 |

(Continued)

OTHER PUBLICATIONS

International Search Report dated Feb. 14, 2013, issued in corresponding International Application No. PCT/EP2012/075915, filed Dec. 18, 2012, 3 pages.

(Continued)

*Primary Examiner* — Eisa Elhilo
(74) *Attorney, Agent, or Firm* — Christensen O'Connor Johnson Kindness PLLC

(57) ABSTRACT

The present invention relates to a composition for dyeing keratin fibres, comprising: one or more oxidation dyes; one or more basifying agents; one or more non-oxyalkylenated fatty substances that are liquid at room temperature in a content of less than or equal to 20% by weight relative to the total weight of the composition; one or more oxidizing agents; one or more oxyethylenated fatty alcohols with a number of oxyethylene units of greater than or equal to 10; one or more oxyethylenated fatty alcohols with a number of oxyethylene units of less than 10; one or more non-oxyethylenated fatty alcohols that are solid at room temperature; and one or more cationic polymers. The present invention also relates to a process for dyeing keratin fibres using such a composition, and also to a kit for preparing the said composition.

17 Claims, No Drawings

(51) Int. Cl.
    *A45D 7/00*          (2006.01)
    *A45D 19/00*        (2006.01)

(56) References Cited

U.S. PATENT DOCUMENTS

| | | |
|---|---|---|
| 2006/0260070 A1 | 11/2006 | Legrand |
| 2010/0172859 A1 | 7/2010 | Matsunaga et al. |
| 2010/0175202 A1* | 7/2010 | Simonet .................. A61K 8/22 |
| | | 8/408 |

FOREIGN PATENT DOCUMENTS

| | | |
|---|---|---|
| EP | 2 377 509 A1 | 10/2011 |
| FR | 2 803 196 A1 | 7/2001 |
| WO | 02/100364 A1 | 12/2002 |
| WO | 2010/070244 A2 | 6/2010 |

OTHER PUBLICATIONS

"EUTANOL® G," Technical Sheet, CASR No. 5333-42-6, Revision No. 04-07-2003, Cognis, Monheim, Germany, Feb. 2, 2004, 2 pages.
"LAMESOFT® PO 65," Technical Sheet, CASR No. 141464-42-8; 68424-61-3, Revision No. 12-10-2003, Cognis, Monheim, Germany, Jan. 26, 2004, 2 pages.

* cited by examiner

COMPOSITION FOR THE OXIDATION DYEING OF KERATIN FIBRES, COMPRISING PARTICULAR FATTY ALCOHOLS, A LIQUID FATTY SUBSTANCE AND A CATIONIC POLYMER

The present invention relates to a composition for dyeing keratin fibres.

Many people have for a long time sought to modify the colour of their hair, and in particular to dye it, for example in order to mask their grey hair.

For the long-lasting colouring of human keratin fibres, "permanent" dyeing methods, also known as oxidation dyeing, have been developed, which use dye compositions containing oxidation dye precursors, which are generally known as oxidation bases. These oxidation bases are colourless or weakly coloured compounds, which, when combined with oxidizing products, may give rise to coloured compounds via a process of oxidative condensation.

It is also known that the shades obtained with these oxidation bases can be varied by combining them with couplers or colouration modifiers. The variety of the molecules used as oxidation bases and couplers allows a rich palette of colours to be obtained.

One of the difficulties encountered during the use of the dyeing processes of the prior art arises from the fact that they are performed under alkaline conditions, and in the presence of oxidizing agents.

In order to improve the performance qualities of processes for dyeing human keratin fibres, and to limit the drawbacks associated with the use of alkaline agents and oxidizing agents, it has been proposed to use in dye compositions a substantial amount of one or more fatty substances.

However, the compositions of the prior art are not entirely satisfactory, and their performance qualities remain to be improved, in particular firstly as regards the working qualities after mixing with an oxidizing composition, especially in terms of texture, ease of application and ease of spreading onto the ends, and secondly as regards the dyeing qualities obtained using these mixtures, especially in terms of the strength and homogeneity of the coloration obtained.

The Applicant has now discovered that the use of certain particular fatty alcohols, in the presence of liquid fatty substances and of cationic polymers, makes it possible to obtain compositions that have improved properties.

A subject of the present invention is thus a composition for dyeing keratin fibres, comprising:
- one or more oxidation dyes,
- one or more basifying agents,
- one or more non-oxyalkylenated fatty substances that are liquid at room temperature, chosen from $C_6$-$C_{16}$ hydrocarbons, hydrocarbons containing more than 16 carbon atoms, non-silicone oils of animal origin, plant oils of triglyceride type, synthetic triglycerides, fluoro oils, fatty alcohols, esters of fatty acids and/or of fatty alcohols other than triglycerides, and silicones, and mixtures thereof, in a content of less than or equal to 20% by weight relative to the total weight of the composition,
- one or more oxidizing agents,
- one or more oxyethylenated fatty alcohols with a number of oxyethylene units of greater than or equal to 10,
- one or more oxyethylenated fatty alcohols with a number of oxyethylene units of less than 10,
- one or more non-oxyethylenated fatty alcohols that are solid at room temperature, and
- one or more cationic polymers.

The composition according to the present invention has very good working qualities. It has a particularly pleasant texture, and good viscosity. It is easy to apply and to spread onto locks of hair, and in particular onto the roots. It does not run and remains localized at the points of application. It spreads easily from the roots to the ends, this spreading occasionally being made useful to prevent overloading with dye. However, even without this spreading, the homogeneity of the colorations obtained is very satisfactory.

Beyond the homogeneity aspect, the composition of the invention also leads to very good dyeing properties. It is particularly effective as regards the strength and also as regards the chromaticity of the colour on the fibres.

Other characteristics and advantages of the invention will emerge more clearly on reading the description and the examples that follow.

In the text hereinbelow, and unless otherwise indicated, the limits of a range of values are included in that range.

The expression "at least one" is equivalent to the expression "one or more".

The human keratin fibres treated via the process according to the invention are preferably the hair.

According to the present invention, the composition comprises one or more basifying agents.

The basifying agent may in particular be a mineral or organic base.

Preferably, the basifying agent is chosen from aqueous ammonia, alkaline carbonates, sodium hydroxide, potassium hydroxide, organic amines, for instance alkanolamines and derivatives thereof, and the compounds of formula (I) below:

(I)

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom, or a $C_1$-$C_6$ alkyl, $C_1$-$C_6$ hydroxyalkyl, or $C_1$-$C_6$ aminoalkyl radical.

Examples of such compounds of formula (I) that may be mentioned include 1,3-diaminopropane, 1,3-diamino-2-propanol, spermine and spermidine.

The basifying agents that are preferred are aqueous ammonia and alkanolamines, and in particular monoethanolamine, diethanolamine and triethanolamine.

In a particularly preferred variant of the invention, the basifying agent is chosen from aqueous ammonia and monoethanolamine, and mixtures thereof.

According to one preferred embodiment of the present invention, the composition does not contain any aqueous ammonia.

According to an also preferred embodiment of the present invention, when the composition contains aqueous ammonia or a salt thereof, it also contains one or more alkanolamines. In this case, the weight amount of alkanolamine(s) in the composition is preferably greater than the weight amount of aqueous ammonia in this same composition.

Generally, the composition has a content of basifying agent(s) ranging from 0.1% to 40% by weight and preferably from 0.5% to 20% by weight relative to the weight of this composition.

Preferably, the composition has a pH greater than or equal to 6, more preferentially a pH ranging from 7 to 12, better still from 8 to 11.5 and even better still from 8 to 11.

This pH may also be adjusted to the desired value by using, in addition to the basifying agent(s), one or more acidifying agents.

Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

The composition according to the invention also comprises one or more oxidation dyes.

The oxidation dyes that may be used in the present invention are generally chosen from oxidation bases, optionally combined with one or more couplers.

The oxidation bases may be chosen especially from para-phenylenediamines, bis(phenyl)alkylenediamines, para-aminophenols, ortho-aminophenols and heterocyclic bases, and their addition salts.

Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl) pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol, 5-acetamido-2-aminophenol and the addition salts thereof.

Among the heterocyclic bases, examples that may be mentioned include pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl) methanol, 2-(3-aminopyrazolo[1,5-a]pyrid-5-yl)ethanol, 2-(3-aminopyrazolo[1,5-a]pyrid-7-yl) ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino] ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and their addition salts.

Mention may be made, among pyrimidine derivatives, of the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-amino ethyl) amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the addition salts thereof. Use may also be made of 4,5-diamino-1-(β-methoxyethyl)pyrazole.

Use will preferably be made of a 4,5-diaminopyrazole and even more preferentially of 4,5-diamino-1-(β-hydroxyethyl) pyrazole and/or a salt thereof.

Mention may also be made, as pyrazole derivatives, of diamino-N,N-dihydropyrazolopyrazolones and in particular those described in application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a] pyrazol-1-one, 2-amino-3-isopropylamino-6,7-dihydro-1H, 5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt thereof.

As heterocyclic bases, use will preferably be made of 4,5-diamino-1-(β-hydroxyethyl)pyrazole and/or 2,3-diamino-6,7-dihydro-1H,5H-pyrazolo[1,2-a]pyrazol-1-one and/or a salt thereof.

The couplers that may be used in the present invention may be chosen from those conventionally used for the dyeing of keratin fibres.

Mention may in particular be made, among these couplers, of meta-phenylenediamines, meta-aminophenols, meta-diphenols, naphthalene-based couplers and heterocyclic couplers, and also their addition salts.

Examples that may be mentioned include 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a] benzimidazole, the addition salts thereof with an acid, and mixtures thereof.

In general, the addition salts of the oxidation bases and couplers that can be used within the context of the invention are especially chosen from the addition salts with an acid such as the hydrochlorides, hydrobromides, sulfates, citrates, succinates, tartrates, lactates, tosylates, benzenesulfonates, phosphates and acetates.

The oxidation base(s) may advantageously represent from 0.0001% to 10% by weight relative to the total weight of the composition, and preferably from 0.005% to 5% by weight relative to the total weight of this composition.

The coupler(s), if they are present, may advantageously represent from 0.0001% to 10% by weight relative to the total weight of the composition, and preferably from 0.005% to 5% by weight relative to the total weight of this composition.

The composition according to the invention also comprises one or more non-oxyalkylenated fatty substances that are liquid at room temperature.

In the present invention, the term "fatty substance" means an organic compound that is insoluble in water at ordinary temperature (25° C.) and at atmospheric pressure (760 mmHg), i.e. which has a solubility in water of less than 5% by weight, preferably less than 1% by weight and even more preferentially less than 0.1% by weight. The fatty substances contain in their structure at least one sequence of at least two siloxane groups or a hydrocarbon-based chain comprising at least 6 carbon atoms. In addition, the fatty substances are generally soluble in organic solvents under the same temperature and pressure conditions, for instance chloroform, ethanol, benzene, liquid petroleum jelly or decamethylcyclopentasiloxane.

The term "liquid fatty substance" means a fatty substance that is liquid at ordinary temperature (25° C.) and at atmospheric pressure (760 mmHg; i.e. $1.013 \times 10^5$ Pa).

The liquid fatty substance(s) are chosen from $C_6$-$C_{16}$ hydrocarbons, hydrocarbons containing more than 16 carbon atoms, non-silicone oils of animal origin, plant oils of triglyceride type, synthetic triglycerides, fluoro oils, fatty alcohols, esters of fatty acids and/or of fatty alcohols other than triglycerides, and silicones, and mixtures thereof.

More particularly, the liquid fatty substance(s) are chosen from:
  linear or branched, optionally cyclic, $C_6$-$C_{16}$ lower hydrocarbons, preferably alkanes. Examples that may be mentioned include hexane, undecane, dodecane, tridecane, and isoparaffins, for instance isohexadecane, isododecane and isodecane,
  linear or branched hydrocarbons of mineral, animal or synthetic origin, containing more than 16 carbon atoms, such as liquid paraffins, liquid petroleum jelly, polydecenes and hydrogenated polyisobutenes such as Parleam®, and squalane.

In one preferred variant, the liquid fatty substance(s) are chosen from liquid paraffin and liquid petroleum jelly.

Preferably, the silicones are chosen from liquid polydialkylsiloxanes, especially liquid polydimethylsiloxanes (PDMS) and liquid polyorganosiloxanes comprising at least one aryl group.

These silicones may also be organomodified. The organomodified silicones that may be used in accordance with the invention are liquid silicones as defined previously, comprising in their structure one or more organofunctional groups attached via a hydrocarbon-based group.

Organopolysiloxanes are defined in greater detail in Walter Noll's *Chemistry and Technology of Silicones* (1968), Academic Press. They can be volatile or non-volatile.

When they are volatile, the silicones are more particularly chosen from those having a boiling point of between 60° C. and 260° C., and more particularly still from:

(i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide or Silbione® 70045 V5 by Rhodia, and dodecamethylcyclopentasiloxane sold under the name Silsoft 1217 by Momentive Performance Materials, and mixtures thereof.

Mention may also be made of cyclocopolymers of the dimethylsiloxane/methylalkylsiloxane type, such as Silicone Volatile® FZ 3109, sold by Union Carbide, of formula:

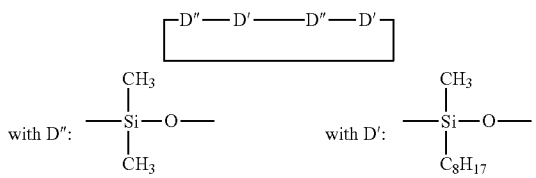

Mention may also be made of mixtures of cyclic polydialkylsiloxanes with organic compounds derived from silicon, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) volatile linear polydialkylsiloxanes having from 2 to 9 silicon atoms and exhibiting a viscosity of less than or equal to $5 \times 10^{-6}$ m$^2$/s at 25° C. An example is decamethyltetrasiloxane, sold in particular under the name SH 200 by Toray Silicone. Silicones coming within this category are also described in the paper published in Cosmetics and Toiletries, Vol. 91, January 76, pp. 27-32, Todd & Byers, *Volatile Silicone Fluids for Cosmetics*. The viscosity of the silicones is measured at 25° C. according to ASTM standard 445 Appendix C.

Non-volatile polydialkylsiloxanes may also be used.

These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:

the Silbione® oils of the 47 and 70 047 series or the Mirasil® oils sold by Rhodia, such as, for example, the oil 70 047 V 500 000;

the oils of the Mirasil® series sold by Rhodia;

the oils of the 200 series from Dow Corning, such as DC200 having a viscosity of 60 000 mm$^2$/s;

the Viscasil® oils from General Electric and certain oils of the SF series (SF 96, SF 18) from General Electric.

Mention may also be made of polydimethylsiloxanes having dimethylsilanol end groups known under the name dimethiconol (CTFA), such as the oils of the 48 series from the company Rhodia.

Among the silicones containing aryl groups are polydiarylsiloxanes, in particular polydiphenylsiloxanes and polyalkylarylsiloxanes. Examples that may be mentioned include the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

certain oils of the SF series from General Electric, such as SF 1023, SF 1154, SF 1250 and SF 1265.

The liquid fatty esters are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one of the alcohol or of the acid from which the esters of the invention result is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention may be made especially of: diethyl sebacate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

The composition may also comprise, as liquid fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars can be monosaccharides, oligosaccharides or polysaccharides.

Mention may be made, as suitable sugars, for example, of sucrose (or saccharose), glucose, galactose, ribose, fucose, maltose, fructose, mannose, arabinose, xylose, lactose and their derivatives, in particular alkyl derivatives, such as methyl derivatives, for example methylglucose.

The esters of sugars and of fatty acids can be chosen in particular from the group consisting of the esters or mixtures of esters of sugars described above and of saturated or unsaturated and linear or branched $C_6$-$C_{30}$ and preferably $C_{12}$-$C_{22}$ fatty acids. If they are unsaturated, these compounds may comprise one to three conjugated or unconjugated carbon-carbon double bonds.

The esters according to this alternative form can also be chosen from mono-, di-, tri- and tetraesters, polyesters and their mixtures.

These esters can, for example, be oleates, laurates, palmitates, myristates, behenates, cocoates, stearates, linoleates, linolenates, caprates, arachidonates or their mixtures, such as, in particular, oleate/palmitate, oleate/stearate or palmitate/stearate mixed esters.

More particularly, use is made of mono- and diesters and in particular mono- or di-oleate, -stearate, -behenate, -oleate/palmitate, -linoleate, -linolenate or -oleate/stearate of sucrose, glucose or methylglucose.

Mention may be made, by way of example, of the product sold under the name Glucate® DO by Amerchol, which is a methylglucose dioleate.

Finally, natural or synthetic esters of monoacids, diacids or triacids with glycerol may also be used.

Among these, mention may be made of plant oils.

As oils of plant origin or synthetic triglycerides that may be used in the composition of the invention as liquid fatty substances, examples that may be mentioned include:
triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, camellia oil, olive oil, caprylic/capric acid triglycerides, for instance those sold by the company Stéarineries Dubois or those sold under the names Miglyol® 810, 812 and 818 by the company Dynamit Nobel, jojoba oil and shea butter oil.

Liquid fatty esters derived from monoalcohols or triglycerides of plant origin will preferably be used as esters according to the invention.

The liquid non-oxyethylenated fatty alcohols that may be used as fatty substances according to the invention advantageously comprise from 8 to 30 carbon atoms.

They may be chosen in particular from unsaturated fatty alcohols and branched saturated fatty alcohols.

These unsaturated liquid fatty alcohols exhibit, in their structures, at least one double or triple bond. Preferably, the fatty alcohols of the invention bear in their structure one or more double bonds. When several double bonds are present, there are preferably 2 or 3 of them and they may or may not be conjugated.

These fatty alcohols may be linear or branched.

They may optionally comprise in their structure at least one aromatic or non-aromatic ring. They are preferably acyclic.

More particularly, the liquid unsaturated fatty alcohols of the invention are selected from oleic (or oleyl) alcohol, linoleic (or linoleyl) alcohol, linolenic (or linolenyl) alcohol and undecylenyl alcohol.

Oleyl alcohol is most particularly preferred.

The liquid fatty alcohols may also be branched saturated fatty alcohols. More particularly, the liquid branched saturated fatty alcohols of the invention are chosen from isostearyl alcohol and octyldodecanol.

Preferably, the fatty substance(s) according to the invention are non-silicone.

They are preferably chosen from liquid fatty substances that are not oxyalkylenated or glycerolated.

According to one preferred embodiment, the liquid fatty substance(s) are chosen from hydrocarbon-based oils comprising more than 6 carbon atoms, such as liquid paraffin; liquid petroleum jelly; esters of $C_1$-$C_{26}$ aliphatic mono acids and of $C_1$-$C_{26}$ aliphatic monoalcohols, these esters having a total number of carbon atoms of greater than or equal to 10, in particular isopropyl myristate and isononyl isononanoate; fatty alcohols such as octyldodecanol; plant oils, in particular avocado oil, camellia oil and olive oil; and mixtures thereof.

Preferably, the content of fatty substances that are liquid at room temperature ranges from 0.5% to 15% by weight and better still from 1% to 10% by weight relative to the total weight of the composition.

According to the present invention, the composition comprises one or more oxidizing agents.

This oxidizing agent may be chosen from the oxidizing agents conventionally used for the oxidation dyeing of keratin fibres, and among which mention may be made of hydrogen peroxide, urea peroxide, alkali metal bromates or ferricyanides, and peroxygenated salts, for instance persulfates, perborates and percarbonates of alkali metals or alkaline-earth metals such as sodium, potassium or magnesium. One or more redox enzymes such as laccases, peroxidases and 2-electron oxidoreductases (such as uricase), optionally in the presence of the respective donor or cofactor thereof, may also be used as oxidizing agent.

The use of hydrogen peroxide is particularly preferred. It may be advantageously used as an aqueous solution (aqueous hydrogen peroxide solution) whose concentration may vary more particularly from 0.1% to 50% by weight, even more preferentially from 0.5% to 20% by weight and better still from 1% to 15% by weight relative to the total weight of the composition.

According to the invention, the composition comprises one or more oxyethylenated fatty alcohols with a number of oxyethylene units of greater than or equal to 10.

Preferably, such a fatty alcohol comprises from 12 to 30 carbon atoms, more preferably 14 to 24 carbon atoms and better still from 16 to 22 carbon atoms.

The number of oxyethylene units is preferably greater than or equal to 15.

Particularly preferred compounds are oxyethylenated cetyl and stearyl alcohols, comprising at least 10, preferably at least 15 and better still at least 20 oxyethylene units.

Preferably, the maximum number of oxyethylene units is 200 and better still 100.

Compounds corresponding to this definition are especially known under the following INCI names: Steareth-20 (stearyl alcohol containing 20 oxyethylene units) and Ceteareth-25 (mixture of cetyl and stearyl alcohols containing 25 oxyethylene units).

Preferably, the content of oxyethylenated fatty substances with a number of oxyethylene units of greater than or equal to 10 ranges from 0.1% to 10% by weight and better still from 1% to 5% by weight relative to the total weight of the composition.

Similarly, the composition of the invention comprises one or more oxyethylenated fatty alcohols with a number of oxyethylene units of less than 10.

Preferably, such a fatty alcohol comprises from 12 to 30 carbon atoms, more preferably 14 to 24 carbon atoms and better still from 16 to 22 carbon atoms.

The number of oxyethylene units is preferably less than or equal to 5.

The number of ethylene oxide units is greater than or equal to 1 and preferably greater than or equal to 2.

Particularly preferred compounds are oxyethylenated cetyl and stearyl alcohols, comprising less than 5 oxyethylene units.

A particularly preferred compound corresponds to the INCI name Steareth-2 (stearyl alcohol containing 2 oxyethylene units).

The content of oxyethylenated fatty alcohols with a number of oxyethylene units of less than 10 is advantageously at least 0.1% by weight. Preferably, the content of oxyethylenated fatty alcohols with a number of oxyethylene units of less than 10 ranges from 0.1% to 10% by weight, better still from 0.2% to 5% by weight and even better still from 0.4% to 2% by weight, relative to the total weight of the composition.

Similarly, the composition of the invention comprises one or more non-oxyethylenated fatty alcohols that are solid at room temperature.

For the purposes of the present invention, the term "fatty alcohol that is solid at room temperature" means a fatty alcohol which is in solid form at ordinary temperature (25° C.) and at atmospheric pressure (760 mmHg; i.e. $1.013 \times 10^5$ Pa).

According to the present invention, the term "fatty alcohol" denotes a compound of formula R—OH in which R denotes a linear or branched, saturated or unsaturated hydrocarbon-based group (i.e. a group consisting of carbon and hydrogen atoms) comprising from 8 to 40 carbon atoms.

Preferably, such a fatty alcohol comprises from 14 to 30 carbon atoms and more preferably from 16 to 24 carbon atoms.

Fatty alcohols corresponding to this definition are especially cetyl alcohol, stearyl alcohol and behenyl alcohol.

The content of non-oxyethylenated fatty alcohols that are solid at room temperature is advantageously at least 0.1% by weight relative to the total weight of the composition. Preferably, the content of non-oxyethylenated fatty alcohols that are solid at room temperature ranges from 0.1% to 20% by weight, better still from 0.5% to 15% by weight and even better still from 1% to 10% by weight relative to the total weight of the composition.

According to the invention, the composition comprises one or more cationic polymers.

The cationic polymer(s) that may be used in accordance with the present invention may be selected from all of those already known per se to enhance the cosmetic properties of hair treated with detergent compositions, these being, in particular, the polymers described in patent application EP-A-0 337 354 and in French patent applications FR-A-2 270 846, 2 383 660, 2 598 611, 2 470 596, 2 519 863 and 2 875 503.

The preferred cationic polymer(s) are chosen from those that contain in their structure units comprising primary, secondary, tertiary and/or quaternary amine groups that may for example either form part of the main polymer chain or be borne by a side substituent directly attached thereto.

Among the cationic polymers that may be mentioned more particularly are polymers of the polyamine, polyaminoamide and polyquaternary ammonium type. Among these polymers, mention may be made of:

(1) Homopolymers or copolymers derived from cross-linked or non-crosslinked acrylic or methacrylic esters or amides and comprising at least one of the units of formula (I), (II), (III) or (IV) below:

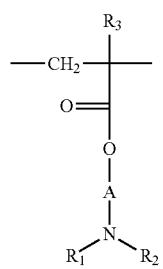

(I)

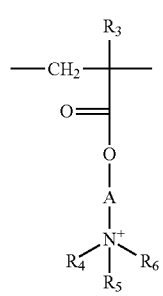

(II)

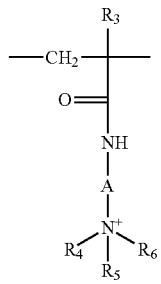

(III)

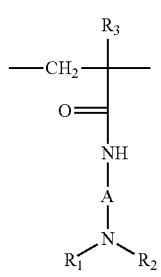

(IV)

in which:

$R_1$ and $R_2$, which are identical or different, each represent a hydrogen atom or an alkyl group having from 1 to 6 carbon atoms, and preferably methyl or ethyl;

$R_3$, which may be identical or different at each occurrence, denotes a hydrogen atom or a $CH_3$ group;

A, which may be identical or different, in each case represents a linear or branched alkyl group of 1 to 6 carbon atoms, preferably 2 or 3 carbon atoms, or a hydroxyalkyl group of 1 to 4 carbon atoms;

$R_4$, $R_5$ and $R_6$, which may be identical or different, each represent an alkyl group containing from 1 to 6 carbon atoms or a benzyl group, and preferably an alkyl group containing from 1 to 6 carbon atoms;

$X^-$ denotes an anion derived from a mineral or organic acid, such as a methosulfate anion or a halide such as chloride or bromide.

The polymers of family (1) can also contain one or more units derived from comonomers which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinyl-caprolactam, and vinyl esters.

Thus, among these polymers of family (1), mention may be made of:

copolymers of acrylamide and of dimethylaminoethyl methacrylate quaternized with dimethyl sulfate or with a dimethyl halide, such as the product sold under the name Hercofloc by the company Hercules, copolymers of acrylamide and of methacryloyloxyethyltrimethylammonium chloride which are described, for example, in patent application EP-A-080 976 and are sold under the name Bina Quat P 100 by the company Ciba Geigy, the copolymer of acrylamide and of methacryloyloxyethyltrimethylammonium methosulfate sold under the name Reten by the company Hercules, quaternized or non-quaternized vinylpyrrolidone/dialkylaminoalkyl acrylate or methacrylate copolymers, such as the products sold under the name Gafquat by the company ISP, such as, for example, Gafquat 734 or Gafquat 755, or alternatively the products known as Copolymer 845, 958 and 937. These polymers are described in detail in French patents 2 077 143 and 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold in particular under the name Styleze CC 10 by ISP, quaternized vinylpyrrolidone/dimethylaminopropylmethacrylamide copolymers such as the product sold under the name Gafquat HS 100 by the company ISP, and the crosslinked polymers of methacryloyloxy($C_1$-$C_4$) alkyl tri($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, more particularly methylenebisacrylamide. A crosslinked acrylamide/methacryloyloxyethyltrimethylammonium chloride copolymer (20/80 by weight) in the form of a dispersion containing 50% by weight of the said copolymer in mineral oil can be used more particularly. This dispersion is sold under the name Salcare® SC 92 by the company Ciba. Use may also be made of a crosslinked homopolymer of methacryloyloxyethyltrimethylammonium chloride containing approximately 50% by weight of the homopolymer in mineral oil or in a liquid ester. These dispersions are sold under the names Salcare® SC 95 and Salcare® SC 96 by the company Ciba.

(2) Cationic polysaccharides in particular chosen from:

a) Cellulose ether derivatives comprising quaternary ammonium groups described in French patent 1 492 597, and in particular the polymers sold under the names JR (JR 400, JR 125, JR 30M) or LR (LR 400, LR 30M) by the company Union Carbide Corporation. These polymers are also defined in the CTFA dictionary as quaternary ammoniums of hydroxyethylcellulose that have reacted with an epoxide substituted with a trimethylammonium group.

b) Cellulose copolymers or cellulose derivatives grafted with a water-soluble quaternary ammonium monomer, described especially in patent U.S. Pat. No. 4,131,576, such as hydroxyalkyl celluloses, for instance hydroxymethyl, hydroxyethyl or hydroxypropyl celluloses grafted especially with a methacryloylethyltrimethylammonium, methacrylamidopropyltrimethylammonium or dimethyldiallylammonium salt.

The commercial products corresponding to this definition are more particularly the products sold under the names Celquat L 200 and Celquat H 100 by the company National Starch.

It is preferred to use a copolymer of hydroxyethylcellulose and of diallyldimethylammonium chloride (Polyquaternium-4), sold, for example, under the name Celquat LOR by the company Akzo Nobel.

c) Guar gums containing trialkylammonium cationic groups. Use is made, for example, of guar gums modified with a 2,3-epoxypropyltrimethylammonium salt (for example, chloride).

Such products are sold in particular under the trade names Jaguar C13 S, Jaguar C 15, Jaguar C 17 or Jaguar C162 by the company Meyhall.

(3) Polymers formed from piperazinyl units and divalent alkylene or hydroxyalkylene radicals containing straight or branched chains, optionally interrupted with oxygen, sulfur or nitrogen atoms or with aromatic or heterocyclic rings, and also the oxidation and/or quaternization products of these polymers. Such polymers are described, in particular, in French patents 2 162 025 and 2 280 361.

(4) Water-soluble cationic polyaminoamides, prepared in particular by polycondensation of an acid compound with a polyamine; these polyaminoamides may be crosslinked with an epihalohydrin, a diepoxide, a saturated or unsaturated dianhydride, a bis-unsaturated derivative, a bis-halohydrin, a bis-azetidinium, a bis-haloacyldiamine or a bis-alkyl halide or else by an oligomer resulting from the reaction of a bifunctional compound which is reactive towards a bis-halohydrin, a bis-azetidinium, a bis-haloacyldiamine, a bis-alkyl halide, an epihalohydrin, a diepoxide or a bis-unsaturated derivative; these polyaminoamides may be alkylated, or quaternized if they contain one or more tertiary amine functions. Such polymers are described, in particular, in French patents 2 252 840 and 2 368 508.

(5) Polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical comprises from 1 to 4 carbon atoms and preferably denotes methyl, ethyl or propyl. Such polymers are especially described in French patent 1 583 363.

Among these derivatives, mention may be made more particularly of the adipic acid/dimethylamino-hydroxypropyl/diethylenetriamine polymers sold under the name Cartaretine F, F4 or F8 by the company Sandoz.

(6) Polymers obtained by reaction of a polyalkylene polyamine containing two primary amine groups and at least one secondary amine group with a dicarboxylic acid chosen from diglycolic acid and saturated aliphatic dicarboxylic acids having from 3 to 6 carbon atoms. The mole ratio between the polyalkylene polyamine and the dicarboxylic acid is between 0.8:1 and 1.4:1; the polyaminoamide resulting therefrom being reacted with epichlorohydrin in a mole ratio of epichlorohydrin relative to the secondary amine group of the polyaminoamide of between 0.5:1 and 1.8:1. Such polymers are described in particular in U.S. Pat. Nos. 3, 227,615 and 2,961,347.

Polymers of this type are sold in particular under the name Hercosett 57 by the company Hercules Inc. or alternatively under the name PD 170 or Delsette 101 by the company Hercules in the case of the adipic acid/epoxypropyl/diethylenetriamine copolymer.

(7) Alkyldiallylamine or dialkyldiallylammonium cyclopolymers, such as the homopolymers or copolymers containing, as the main constituent of the chain, units conforming to the formula (V) or (VI):

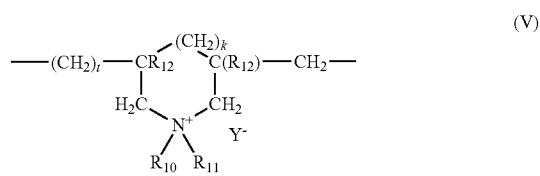

-continued

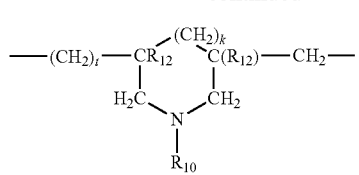
(VI)

in which k and t are equal to 0 or 1, the sum k+t being equal to 1; $R_{12}$ denotes a hydrogen atom or a methyl group; $R_{10}$ and $R_{11}$, independently of one another, denote an alkyl group having from 1 to 6 carbon atoms, a hydroxyalkyl group in which the alkyl group has preferably 1 to 5 carbon atoms, a lower amidoalkyl group (i.e. the alkyl part of which is $C_1$-$C_4$), or else $R_{10}$ and $R_{11}$ may, together with the nitrogen atom to which they are attached, denote heterocyclic groups, such as piperidyl or morpholinyl; $Y^-$ is an anion such as bromide, chloride, acetate, borate, citrate, tartrate, bisulfate, bisulfite, sulfate or phosphate. These polymers are in particular described in French patent 2 080 759 and in its Certificate of Addition 2 190 406.

Preferably, $R_{10}$ and $R_{11}$ each denote, independently of one another, an alkyl group having from 1 to 4 carbon atoms.

Among the polymers defined above, mention may be made of dialkyldiallylammonium chloride homopolymers, more particularly dimethyldiallylammonium chloride homopolymer (INCI name: Polyquaternium-6) sold, for example, under the name Merquat® 100 by the company Nalco (and homologues thereof of low weight-average molecular masses) and dialkyldiallylammonium chloride copolymers, more particularly the copolymer of dimethyldiallylammonium chloride and of acrylamide sold under the name Merquat® 550.

(8) The quaternary diammonium polymers containing repeating units corresponding to formula (VII):

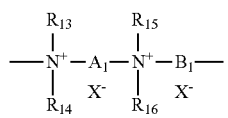
(VII)

in which:

$R_{13}$, $R_{14}$, $R_{15}$ and $R_{16}$, which may be identical or different, represent aliphatic, alicyclic or arylaliphatic groups containing from 1 to 6 carbon atoms or lower hydroxyalkylaliphatic groups (i.e. the alkyl part of which is $C_1$-$C_4$), or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ each represent a linear or branched $C_1$-$C_6$ alkyl group substituted with a nitrile, ester, acyl or amide group or a —CO—O—$R_{17}$-E or —CO—NH—$R_{17}$-E group where $R_{17}$ is an alkylene group and E is a quaternary ammonium group;

$A_1$ and $B_1$ represent polymethylene groups containing from 2 to 8 carbon atoms, which may be linear or branched and saturated or unsaturated and may contain, joined to or intercalated in the main chain, one or more aromatic rings, or one or more oxygen or sulfur atoms or sulfoxide, sulfone, disulfide, amino, alkylamino, hydroxyl, quaternary ammonium, ureido, amide or ester groups; and $X^-$ denotes an anion derived from a mineral or organic acid; $A_1$, $R_{13}$ and $R_{15}$ may, with the two nitrogen atoms to which they are attached, form a piperazine ring; moreover, if $A_1$ denotes a linear or branched, saturated or unsaturated alkylene or hydroxyalkylene group, $B_1$ may also denote a group:

—(CH$_2$)$_n$—CO-E'-OC—(CH$_2$)$_n$— in which n denotes an integer from 0 to 7 and E' denotes:

a) a glycol residue of formula —O—Z—O—, in which Z denotes a linear or branched hydrocarbon-based group, or a group corresponding to one of the following formulae:

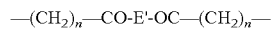

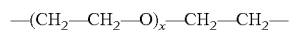

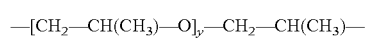

in which x and y each denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula —NH—Y—NH—, in which Y denotes a linear or branched hydrocarbon-based group, or alternatively the divalent group —CH$_2$—CH$_2$—S—S—CH$_2$—CH$_2$—;

d) a ureylene group of formula —NH—CO—NH—.

Preferably, $X^-$ is an anion such as chloride or bromide.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Use may more particularly be made of the polymers which consist of repeating units corresponding to formula (VIII):

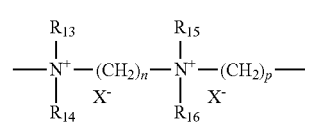
(VIII)

in which $R_{13}$, $R_{14}$, $R_{15}$ and $R_{16}$, which may be identical or different, each denote an alkyl or hydroxyalkyl group having from 1 to 4 carbon atoms approximately, n and p are integers ranging from 2 to 20 and preferably from 2 to 8, and $X^-$ is an anion derived from a mineral or organic acid. Preferably, $R_{13}$, $R_{14}$, $R_{15}$ and $R_{16}$ each denote a methyl group. As an example of a polymer that may be used corresponding to formula (VIII), mention may be made of hexadimethrine chloride, sold under the name Mexomer PO by the company Chimex.

(9) Polyquaternary ammonium polymers consisting of units of formula (IX):

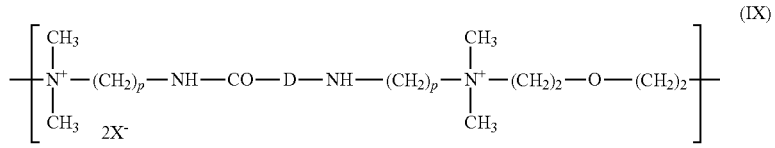

in which:
p denotes an integer ranging from 1 to 6 approximately;
D may be nothing or may represent a group
—(CH$_2$)$_r$—CO— in which r denotes a number equal to 4 or 7, and
X$^-$ denotes an anion derived from a mineral or organic acid.

Cationic polymers comprising units of formula (IX) are in particular described in patent application EP-A-122 324 and may be prepared according to the processes described in U.S. Pat. Nos. 4,157,388, 4,390,689, 4,702,906 and 4,719,282.

Among these polymers, the ones that are preferred are those with a molecular mass, measured by carbon-13 NMR, of less than 100 000, and in the formula of which:

p is equal to 3, and a) D represents a group —(CH$_2$)$_4$—CO—, X denotes a chlorine atom, the molecular mass measured by carbon-13 NMR ($^{13}$C NMR) being about 5600; a polymer of this type is sold by the company Miranol under the name Mirapol-AD1, b) D represents a group —(CH$_2$)$_7$—CO—, X denotes a chlorine atom, the molecular mass measured by carbon-13 NMR ($^{13}$C NMR) being about 8100; a polymer of this type is sold by the company Miranol under the name Mirapol-AZ1, c) D denotes the value zero, X denotes a chlorine atom, the molecular weight measured by carbon-13 NMR ($^{13}$C NMR) being around 25 500; a polymer of this type is sold by the company Miranol under the name Mirapol-A15, d) a "block copolymer" formed from units corresponding to the polymers described in paragraphs a) and c), sold by the company Miranol under the names Mirapol-9 ($^{13}$C NMR molecular mass of about 7800), Mirapol-175 ($^{13}$C NMR molecular mass of about 8000) and Mirapol-95 ($^{13}$C NMR molecular mass of about 12 500).

Even more particularly, the polymer containing units of formula (IX) in which p is equal to 3, D denotes the value zero and X denotes a chlorine atom, the molecular mass measured by carbon-13 NMR ($^{13}$C NMR) being about 25 500, is preferred according to the invention.

(10) Quaternary polymers of vinylpyrrolidone and of vinylimidazole, for instance the products sold under the names Luviquat FC 905, FC 550 and FC 370 by the company BASF.

(11) Ethoxylated cationic tallow polyamines such as Polyquart H sold by Henkel, referred to under the name Polyethylene Glycol (15) Tallow Polyamine in the CTFA dictionary.

(12) Vinylamide homopolymers or copolymers and in particular partially hydrolysed vinylamide homopolymers such as poly(vinylamine/vinylamides). These polymers are formed from at least one vinylamide monomer corresponding to the following formula:

in which R, R$^1$ and R$^2$ are each chosen from a hydrogen atom, a C$_1$-C$_{20}$ alkyl group, an aryl group and an alkylaryl group, the alkyl part of which comprises from 1 to 20 carbon atoms.

In particular, the said monomer may be chosen from N-vinylformamide, N-methyl-N-vinylacetamide and N-vinylacetamide. Preferably, use is made of the poly(vinylamine/N-vinylformamide) as sold under the name Catiofast VMP by the company BASF or under the name Lupamin 9030 by the company BASF.

These polymers may be formed, for example, by radical polymerization of a vinylamide monomer followed by partial acidic or basic hydrolysis of the amide functions to quaternizable amine functions, as described in patent applications WO 2007/005 577, U.S. Pat. Nos. 5,374,334, 6,426,383 and 6,894,110.

(13) Cationic polyurethanes.

Among the cationic polyurethanes, use is preferably made of the polyurethanes formed by the following monomers:

(a1) at least one N-methyldiethanolamine (noted NMDEA), (a2) at least one ethylene/butylene nonionic copolymer as sold under the name Krasol LBH-P 2000, and (b) at least one isophorone diisocyanate (noted IPDI).

Preferably, the amines forming the cationic units (a1) represent from 0.1% to 50%, in particular from 1% to 30% and better still from 5% to 20% by weight relative to the total weight of the final polyurethane.

These polyurethanes and the syntheses thereof are described, for example, in patent application FR-A-2 898 603.

(14) Other cationic polymers that may be used in the context of the invention are cationic proteins or cationic protein hydrolysates, polyalkyleneimines, in particular polyethyleneimines, polymers containing vinylpyridine or vinylpyridinium units, and chitin derivatives.

Among all the cationic polymers that may be used in the context of the present invention, use is preferably made of the alkyldiallylamine or dialkyldiallylammonium cyclopolymers of family (7), and more particularly dimethyldiallylammonium chloride homopolymer (INCI name: Polyquaternium-6), and also the quaternary diammonium polymers of family (8), and more particularly those consisting of repeating units corresponding to formula (VIII) above, especially such as hexadimethrine chloride.

The composition of the invention contains one or more cationic polymers in a content preferably ranging from 0.01% to 10% by weight, more preferentially from 0.1% to 5% by weight and better still from 0.5% to 3% by weight relative to the total weight of the composition.

According to the invention, in addition to the oxidation dye(s), the composition may also comprise one or more direct dyes.

The direct dyes that may be used in the composition are more particularly chosen from ionic and nonionic species, preferably cationic or nonionic species.

Examples of suitable direct dyes that may be mentioned include azo dyes; methine dyes; carbonyl dyes; azine dyes;

nitro(hetero)aryl dyes; tri(hetero)arylmethane dyes; porphyrin dyes; phthalocyanin dyes, and natural direct dyes, alone or as mixtures.

More particularly, the azo dyes comprise an —N=N— function in which the two nitrogen atoms are not simultaneously engaged in a ring. However, it is not excluded for one of the two nitrogen atoms of the sequence —N=N— to be engaged in a ring.

The dyes of the methine family are more particularly compounds comprising at least one sequence chosen from >C=C< and —N=C< in which the two atoms are not simultaneously engaged in a ring. However, it is pointed out that one of the nitrogen or carbon atoms of the sequences may be engaged in a ring. More particularly, the dyes of this family are derived from compounds of the type such as methines, azomethines, monoarylmethanes and diarylmethanes, indoamines (or diphenylamines), indophenols, indoanilines, carbocyanins, azacarbocyanins and isomers thereof, diazacarbocyanins and isomers thereof, tetraazacarbocyanins and hemicyanins.

As regards the dyes of the carbonyl family, examples that may be mentioned include dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazo lone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin.

As regards the dyes of the cyclic azine family, mention may be made especially of azine, xanthene, thioxanthene, fluorindine, acridine, (di)oxazine, (di)thiazine and pyronin.

The nitro(hetero)aromatic dyes are more particularly nitrobenzene or nitropyridine direct dyes.

As regards the dyes of porphyrin or phthalocyanin type, it is possible to use cationic or non-cationic compounds, optionally comprising one or more metals or metal ions, for instance alkali metals, alkaline-earth metals, zinc and silicon.

Examples of particularly suitable direct dyes that may be mentioned include nitrobenzene dyes; azo direct dyes; azomethine direct dyes; methine direct dyes; azacarbocyanin direct dyes, for instance tetraazacarbocyanins (tetraazapentamethines); quinone and in particular anthraquinone, naphthoquinone or benzoquinone direct dyes; azine direct dyes; xanthene direct dyes; triarylmethane direct dyes; indoamine direct dyes; indigoid direct dyes; phthalocyanin direct dyes, porphyrin direct dyes and natural direct dyes, alone or as mixtures.

Mention may be made, among the natural direct dyes which can be used according to the invention, of lawsone, juglone, alizarin, purpurin, carminic acid, kermesic acid, purpurogallin, protocatechaldehyde, indigo, isatin, curcumin, spinulosin, apigenidin and orceins. Use may also be made of extracts or decoctions comprising these natural dyes and in particular henna-based poultices or extracts.

When they are present, the direct dye(s) advantageously represent from 0.0001% to 10% by weight and preferably from 0.005% to 5% by weight relative to the total weight of the composition.

The composition according to the present invention may also comprise one or more surfactants other than the oxyethylenated fatty alcohols of the invention.

In particular, the surfactant(s) are chosen from anionic, amphoteric, zwitterionic, cationic and nonionic surfactants.

The term "anionic surfactant" means a surfactant comprising, as ionic or ionizable groups, only anionic groups. These anionic groups are preferably chosen from the groups —C(O)OH, —C(O)O—, —SO$_3$H, —S(O)$_2$O—, —OS(O)$_2$OH, —OS(O)$_2$O—, —P(O)OH$_2$, —P(O)$_2$O—, —P(O)O$_2$—, —P(OH)$_2$, =P(O)OH, —P(OH)O—, =P(O)O—, =POH, =PO—, the anionic parts comprising a cationic counterion such as an alkali metal, an alkaline-earth metal or an ammonium.

As examples of anionic surfactants that may be used in the composition according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglycoside polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 24 carbon atoms and the aryl group denoting a phenyl group.

These compounds can be oxyethylenated and then preferably comprise from 1 to 50 ethylene oxide units.

The salts of $C_6$-$C_{24}$ alkyl monoesters of polyglycoside-polycarboxylic acids can be selected from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Use is preferably made of alkali metal or alkaline-earth metal salts and in particular of sodium or magnesium salts.

Among the anionic surfactants mentioned, use is preferably made of ($C_6$-$C_{24}$)alkyl sulfates, ($C_6$-$C_{24}$)alkyl ether sulfates comprising from 2 to 50 ethylene oxide units, especially in the form of alkali metal, ammonium, amino alcohol and alkaline-earth metal salts, or a mixture of these compounds.

In particular, use is preferably made of ($C_{12}$-$C_{20}$)alkyl sulfates, ($C_{12}$-$C_{20}$)alkyl ether sulfates comprising from 2 to 20 ethylene oxide units, especially in the form of alkali metal, ammonium, amino alcohol and alkaline-earth metal salts, or a mixture of these compounds. Better still, it is preferable to use sodium lauryl ether sulfate comprising 2.2 mol of ethylene oxide.

The amphoteric or zwitterionic surfactant(s), which are preferably (a) non-silicone surfactant(s), which can be used in the present invention can in particular be derivatives of secondary or tertiary, optionally quaternized aliphatic amines, in which derivatives the aliphatic group is a linear or branched chain comprising from 8 to 22 carbon atoms, the said amine derivatives comprising at least one anionic group, such as, for example, a carboxylate, sulfonate, sulfate, phosphate or phosphonate group. Mention may be made in particular of $(C_8-C_{20})$alkylbetaines, sulfobetaines, $(C_8-C_{20})$alkylamido$(C_3-C_8)$alkylbetaines and $(C_8-C_{20})$alkylamido$(C_6-C_8)$alkylsulfobetaines.

Among the secondary or tertiary, optionally quaternized aliphatic amine derivatives that can be used, as defined above, mention may also be made of the compounds of respective structures (A1) and (A2):

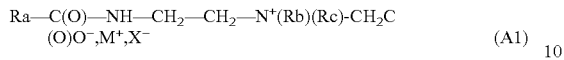

(A1)

in which formula (A1):

Ra represents a $C_{10}-C_{30}$ alkyl or alkenyl group derived from an acid RaCOOH preferably present in hydrolysed coconut oil, or a heptyl, nonyl or undecyl group;

Rb represents a β-hydroxyethyl group; and

Rc represents a carboxymethyl group;

$M^+$ represents a cationic counterion derived from an alkali metal or alkaline-earth metal, such as sodium, an ammonium ion or an ion derived from an organic amine, and $X^-$ represents an organic or inorganic anionic counterion, such as that chosen from halides, acetates, phosphates, nitrates, $(C_1-C_4)$alkyl sulfates, $(C_1-C_4)$alkyl- or $(C_1-C_4)$ alkylaryl-sulfonates, in particular methyl sulfate and ethyl sulfate; or alternatively $M^+$ and $X^-$ are absent;

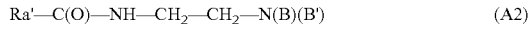

(A2)

in which formula (A2):

B represents the group —$CH_2$—$CH_2$—O—X';

B' represents the group —$(CH_2)_zY'$, with z=1 or 2;

X' represents the group —$CH_2$—C(O)OH, —$CH_2$—C(O)OZ', —$CH_2$—$CH_2$—C(O)OH, or —$CH_2$—$CH_2$—C(O)OZ', or a hydrogen atom;

Y' represents the group —C(O)OH, —C(O)OZ', —$CH_2$—CH(OH)—$SO_3$H or the group —$CH_2$—CH(OH)—$SO_3$—Z';

Z' represents a cationic counterion derived from an alkali metal or alkaline-earth metal, such as sodium, an ammonium ion or an ion derived from an organic amine;

Ra' represents a $C_{10}-C_{30}$ alkyl or alkenyl group of an acid Ra'—C(O)OH preferably present in coconut oil or in hydrolysed linseed oil, an alkyl group, especially of $C_{17}$ and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Among the amphoteric or zwitterionic surfactants mentioned above, use is preferably made of $(C_8-C_{20})$alkylbetaines such as cocoylbetaine, $(C_8-C_{20})$alkylamido$(C_3-C_8)$ alkylbetaines such as cocamidopropylbetaine, and mixtures thereof. More preferentially, the amphoteric or zwitterionic surfactant(s) are chosen from cocamidopropylbetaine and cocobetaine.

The cationic surfactant(s) which can be used in the composition according to the invention comprise, for example, salts of optionally polyoxyalkylenated primary, secondary or tertiary fatty amines, quaternary ammonium salts, and their mixtures.

Examples of quaternary ammonium salts that may especially be mentioned include:

those corresponding to the general formula (A3) below:

(A3)

in which formula (A3):

R8 to R11, which may be identical or different, represent a linear or branched aliphatic group comprising from 1 to 30 carbon atoms, or an aromatic group such as aryl or alkylaryl, it being understood that at least one of the groups R8 to R11 comprises from 8 to 30 carbon atoms and preferably from 12 to 24 carbon atoms; and $X^-$ represents an organic or inorganic anionic counterion, such as that chosen from halides, acetates, phosphates, nitrates, $(C_1-C_4)$alkyl sulfates, $(C_1-C_4)$alkyl- or $(C_1-C_4)$ alkylaryl-sulfonates, in particular methyl sulfate and ethyl sulfate.

The aliphatic groups of R8 to R11 may also comprise heteroatoms especially such as oxygen, nitrogen, sulfur and halogens.

The aliphatic groups of R8 to R11 are chosen, for example, from $C_1-C_{30}$ alkyl, $C_1-C_{30}$ alkoxy, polyoxy$(C_2-C_6)$ alkylene, $C_1-C_{30}$ alkylamide, $(C_{12}-C_{22})$alkylamido$(C_2-C_6)$ alkyl, $(C_{12}-C_{22})$alkylacetate, $C_1-C_{30}$ hydroxyalkyl, $X^-$ is an anionic counterion chosen from halides, phosphates, acetates, lactates, $(C_1-C_4)$alkyl sulfates, and $(C_1-C_4)$alkyl- or $(C_1-C_4)$alkylaryl-sulfonates.

Among the quaternary ammonium salts of formula (A3), preference is given firstly to tetraalkylammonium chlorides, for instance dialkyldimethylammonium or alkyltrimethylammonium chlorides in which the alkyl group contains approximately from 12 to 22 carbon atoms, in particular behenyltrimethylammonium chloride, distearyldimethylammonium chloride, cetyltrimethylammonium chloride, benzyldimethylstearylammonium chloride, or else, secondly, distearoylethylhydroxyethylmethylammonium methosulfate, dipalmitoylethylhydroxyethylammonium methosulfate or distearoylethylhydroxyethylammonium methosulfate, or else, lastly, palmitylamidopropyltrimethylammonium chloride or stearamidopropyl-dimethyl(myristyl acetate)ammonium chloride, sold under the name Ceraphyl® 70 by the company Van Dyk;

quaternary ammonium salts of imidazoline, for instance those of formula (A4) below:

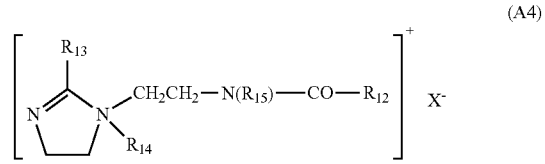

(A4)

in which formula (A4):

R12 represents an alkenyl or alkyl group comprising from 8 to 30 carbon atoms, for example tallow fatty acid derivatives;

R13 represents a hydrogen atom, a $C_1-C_4$ alkyl radical or an alkenyl or alkyl radical containing from 8 to 30 carbon atoms;

R14 represents a $C_1-C_4$ alkyl group;

R15 represents a hydrogen atom or a $C_1-C_4$ alkyl group;

X⁻ represents an organic or inorganic anionic counterion, such as that chosen from halides, phosphates, acetates, lactates, ($C_1$-$C_4$)alkyl sulfates, ($C_1$-$C_4$)alkyl- or ($C_1$-$C_4$) alkylaryl-sulfonates.

$R_{12}$ and $R_{13}$ preferably denote a mixture of alkyl or alkenyl groups comprising from 12 to 21 carbon atoms, for example tallow fatty acid derivatives, $R_{14}$ denotes a methyl group, and $R_{15}$ denotes a hydrogen atom. Such a product is sold, for example, under the name Rewoquat® W 75 by the company Rewo;

di- or triquaternary ammonium salts, in particular of formula (A5) below:

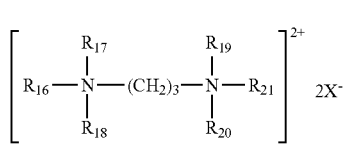

(A5)

in which formula (A5):

R16 denotes an alkyl group comprising approximately from 16 to 30 carbon atoms, which is optionally hydroxylated and/or interrupted with one or more oxygen atoms;

R17 is chosen from hydrogen, an alkyl group comprising from 1 to 4 carbon atoms or a group —(CH₂)₃—N⁺(R16a)(R17a)(R18a), X⁻;

R16a, R17a, R18a, R18, R19, R20 and R21, which may be identical or different, are chosen from hydrogen and an alkyl group comprising from 1 to 4 carbon atoms; and X⁻, which may be identical or different, represents an organic or inorganic anionic counterion, such as that chosen from halides, acetates, phosphates, nitrates, ($C_1$-$C_4$)alkyl sulfates, ($C_1$-$C_4$)alkyl- or ($C_1$-$C_4$)alkylaryl-sulfonates, in particular methyl sulfate and ethyl sulfate.

Such compounds are, for example, Finquat CT-P, provided by Finetex (Quaternium 89), or Finquat CT, provided by Finetex (Quaternium 75);

quaternary ammonium salts containing one or more ester functions, such as those of formula (A6) below:

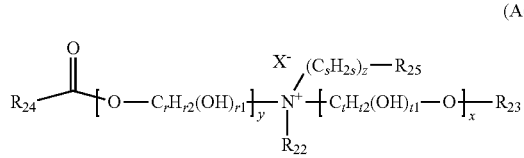

(A6)

in which formula (A6):

$R_{22}$ is chosen from $C_1$-$C_6$ alkyl and $C_1$-$C_6$ hydroxyalkyl or dihydroxyalkyl groups, $R_{23}$ is selected from:
the group

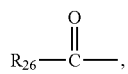

linear or branched, saturated or unsaturated $C_1$-$C_{22}$ hydrocarbon-based groups R27, a hydrogen atom, $R_{25}$ is selected from:
the group

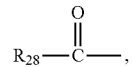

the groups R29, which are linear or branched, saturated or unsaturated $C_1$-$C_6$ hydrocarbon-based radicals;

a hydrogen atom, $R_{24}$, $R_{26}$ and $R_{28}$, which are identical or different, are selected from linear or branched, saturated or unsaturated $C_7$-$C_{21}$ hydrocarbon radicals;

r, s and t, which may be identical or different, are integers ranging from 2 to 6, r1 and t1, which may be identical or different, are equal to 0 or 1, with r2+r1=2r and t1+t2=2t, y is an integer ranging from 1 to 10, x and z, which may be identical or different, are integers ranging from 0 to 10, X⁻ represents an organic or inorganic anionic counterion, with the proviso that the sum x+y+z is from 1 to 15, that when x is 0, then $R_{23}$ denotes $R_{27}$ and that when z is 0, then $R_{25}$ denotes $R_{29}$.

The alkyl groups R22 may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and may have 12 to 22 carbon atoms, or may be short and may have from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

y is advantageously equal to 1.

Preferably, r, s and t, which may be identical or different, equal 2 or 3, and even more particularly are equal to 2.

The anionic counterion X⁻ is preferably a halide, such as chloride, bromide or iodide; a ($C_1$-$C_4$)alkyl sulfate or a ($C_1$-$C_4$)alkyl- or ($C_1$-$C_4$)alkylaryl-sulfonate. However, it is possible to use methanesulfonate, phosphate, nitrate, tosylate, an anion derived from an organic acid, such as acetate or lactate, or any other anion that is compatible with the ammonium containing an ester function.

The anionic counterion X⁻ is even more particularly chloride, methyl sulfate or ethyl sulfate.

Use is made more particularly in the composition according to the invention of the ammonium salts of formula (A6) in which:

R22 denotes a methyl or ethyl group, x and y are equal to 1, z is equal to 0 or 1, r, s and t are equal to 2, R23 is chosen from:
the group

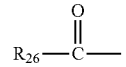

methyl, ethyl or $C_{14}$-$C_{22}$ hydrocarbon-based groups,
a hydrogen atom,
R25 is chosen from:

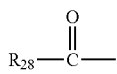

the group
a hydrogen atom,
R24, R26 and R28, which may be identical or different, are chosen from linear or branched, saturated or unsaturated $C_{13}$-$C_{17}$ hydrocarbon-based groups, and more particularly from linear or branched, saturated or unsaturated $C_{13}$-$C_{17}$ alkyl and alkenyl groups.

Advantageously, the hydrocarbon-based radicals are linear.

Among the compounds of formula (A6), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably have from 14 to 18 carbon atoms and originate more particularly from a vegetable oil, such as palm oil or sunflower oil. When the compound comprises several acyl groups, the latter can be identical or different.

These products are obtained, for example, by direct esterification of triethanolamine, triisopropanolamine, an alkyldiethanolamine or an alkyldiisopropanolamine, which are optionally oxyalkylenated, with fatty acids or with mixtures of fatty acids of vegetable or animal origin, or by transesterification of their methyl esters. This esterification is followed by a quaternization by means of an alkylating agent, such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium salts of monoesters, diesters and triesters with a weight majority of diester salts.

It is also possible to use the ammonium salts containing at least one ester function that are described in patents U.S. Pat. Nos. 4,874,554 and 4,137,180.

Use may be made of behenoylhydroxypropyltrimethylammonium chloride sold by KAO under the name Quatarmin BTC 131.

Preferably, the ammonium salts containing at least one ester function contain two ester functions.

Among the cationic surfactants that may be present in the composition according to the invention, it is more particularly preferred to choose cetyltrimethylammonium, behenyltrimethylammonium and dipalmitoylethyl-hydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

Examples of nonionic surfactants that can be used in the composition used according to the invention are described,
for example, in the *Handbook of Surfactants* by M. R. Porter, published by Blackie & Son (Glasgow and London), 1991, pp. 116-178. They are especially chosen from polyethoxylated, polypropoxylated or polyglycerolated ($C_1$-$C_{20}$) alkylphenols containing at least one fatty chain comprising, for example, from 8 to 18 carbon atoms, the number of ethylene oxide and/or propylene oxide groups possibly ranging especially from 2 to 50, and the number of glycerol groups possibly ranging especially from 2 to 30.

Mention may also be made of copolymers of ethylene oxide and propylene oxide, optionally oxyethylenated sorbitan fatty acid esters, sucrose fatty acid esters, polyoxyalkylenated fatty acid esters, optionally oxyalkylenated alkyl polyglycosides, alkyl glucoside esters, derivatives of N-alkylglucamine and of N-acylmethylglucamine, aldobionamides and amine oxides.

The additional nonionic surfactants are chosen more particularly from mono- or polyoxyalkylenated or mono- or polyglycerolated nonionic surfactants. The oxyalkylene units are more particularly oxyethylene or oxypropylene units, or a combination thereof, preferably oxyethylene units.

Examples of additional oxyalkylenated nonionic surfactants that may be mentioned include:
oxyalkylenated ($C_8$-$C_{24}$)alkylphenols;
saturated or unsaturated, linear or branched, oxyalkylenated $C_8$-$C_{30}$ amides;
esters of saturated or unsaturated, linear or branched, $C_8$-$C_{30}$ acids and of polyethylene glycols;
polyoxyethylenated esters of saturated or unsaturated, linear or branched, $C_8$-$C_{30}$ acids and of sorbitol;
saturated or unsaturated, oxyethylenated plant oils,
condensates of ethylene oxide and/or of propylene oxide, inter alia, alone or as mixtures;
oxyethylenated and/or oxypropylenated silicones.

The surfactants preferably contain a number of moles of ethylene oxide and/or of propylene oxide of between 1 and 100, preferably between 2 and 50 and preferably between 2 and 30. Advantageously, the nonionic surfactants do not comprise any oxypropylene units.

In accordance with a preferred embodiment of the invention, the oxyalkylenated nonionic surfactants are chosen from polyoxyethylenated esters of linear or branched, saturated or unsaturated $C_8$-$C_{30}$ acids and of sorbitol comprising from 1 to 100 mol of ethylene oxide.

As examples of mono- or polyglycerolated nonionic surfactants, preference is given to using mono- or polyglycerolated $C_8$-$C_{40}$ alcohols.

More particularly, the mono- or polyglycerolated $C_8$-$C_{40}$ alcohols correspond to formula (A7) below:

$$R29O\text{—}[CH_2\text{—}CH(CH_2OH)\text{—}O]m\text{-}H \quad (A7)$$

in which formula (A7):
R29 represents a linear or branched $C_8$-$C_{40}$ and preferably $C_8$-$C_{30}$ alkyl or alkenyl radical; and
m represents a number ranging from 1 to 30 and preferably from 1 to 10.

As examples of compounds of formula (A7) that are suitable within the context of the invention, mention may be made of lauryl alcohol containing 4 mol of glycerol (INCI name: Polyglyceryl-4 Lauryl Ether), lauryl alcohol comprising 1.5 mol of glycerol, oleyl alcohol comprising 4 mol of glycerol (INCI name: Polyglyceryl-4 Oleyl Ether), oleyl alcohol comprising 2 mol of glycerol (INCI name: Polyglyceryl-2 Oleyl Ether), cetearyl alcohol comprising 2 mol of glycerol, cetearyl alcohol comprising 6 mol of glycerol, oleocetyl alcohol comprising 6 mol of glycerol, and octadecanol comprising 6 mol of glycerol.

The mono- or polyglycerolated alcohol of formula (A7) may represent a mixture of alcohols in the same way that the value of m represents a statistical value, which means that, in a commercial product, several species of polyglycerolated fatty alcohols may coexist in the form of a mixture.

Among the mono- or polyglycerolated alcohols, it is preferred more particularly to use a $C_8/C_{10}$ alcohol with one mole of glycerol, a $C_{10}/C_{12}$ alcohol with 1 mol of glycerol and a $C_{12}$ alcohol with 1.5 mol of glycerol.

Preferably, the additional surfactant(s) are chosen from nonionic surfactants and from anionic surfactants. More particularly, the surfactant(s) present in the composition are chosen from nonionic surfactants.

In the composition of the invention, the amount of additional surfactant(s) other than the oxyethylenated fatty alcohols preferably ranges from 0.1% to 50% by weight and better still from 0.5% to 20% by weight relative to the total weight of the composition.

The composition according to the present invention may also comprise one or more mineral thickeners chosen from organophilic clays and fumed silicas, or mixtures thereof.

The organophilic clay may be chosen from montmorillonite, bentonite, hectorite, attapulgite and sepiolite, and mixtures thereof. The clay is preferably a bentonite or a hectorite.

These clays can be modified with a chemical compound chosen from quaternary ammoniums, tertiary amines, amine acetates, imidazolines, amine soaps, fatty sulfates, alkylarylsulfonates and amine oxides, and mixtures thereof.

Mention may be made, as organophilic clays, of quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; and quaternium-18/benzalkonium bentonites, such as those sold under the names Claytone HT and Claytone PS by Southern Clay.

The fumed silicas can be obtained by high-temperature pyrolysis of a volatile silicon compound in an oxyhydrogen flame, producing a finely divided silica. This process makes it possible especially to obtain hydrophilic silicas having a large number of silanol groups at their surface. Such hydrophilic silicas are sold, for example, under the names Aerosil 130®, Aerosil 200®, Aerosil 255®, Aerosil 300® and Aerosil 380® by the company Degussa, and Cab-O-Sil HS-5®, Cab-O-Sil EH-5®, Cab-O-Sil LM-130®, Cab-O-Sil MS-55® and Cab-O-Sil M-5® by the company Cabot.

It is possible to chemically modify the surface of the silica via chemical reaction in order to reduce the number of silanol groups. It is possible in particular to replace silanol groups with hydrophobic groups: a hydrophobic silica is then obtained.

The hydrophobic groups can be:
trimethylsiloxyl groups, which are obtained in particular by treating fumed silica in the presence of hexamethyldisilazane. Silicas thus treated are known as "Silica silylate" according to the CTFA (6th Edition, 1995). They are sold, for example, under the references Aerosil R812® by the company Degussa and Cab-O-Sil TS-530® by the company Cabot.
dimethylsilyloxy or polydimethylsiloxane groups, which are obtained in particular by treating fumed silica in the presence of polydimethylsiloxane or dimethyldichlorosilane. Silicas thus treated are known as "silica dimethyl silylate" according to the CTFA (6th Edition, 1995). They are sold, for example, under the references Aerosil R972® and Aerosil R974® by the company Degussa, and Cab-O-Sil TS-610® and Cab-O-Sil TS-720® by the company Cabot.

The fumed silica preferably exhibits a particle size which can be nanometric to micrometric, for example ranging from approximately 5 to 200 nm.

The preferred mineral thickeners are chosen from hectorites, organomodified bentonites and optionally modified fumed silicas.

When it is present, the mineral thickener preferably represents from 1% to 30% by weight relative to the weight of the composition.

The composition according to the present invention may also comprise one or more organic thickeners.

These thickeners may be chosen from fatty acid amides (coconut monoethanolamide or diethanolamide, oxyethylenated alkyl ether carboxylic acid monoethanolamide), polymeric thickeners such as cellulose-based thickeners (hydroxyethyl cellulose, hydroxypropyl cellulose or carboxymethyl cellulose), guar gum and derivatives thereof (hydroxypropyl guar), gums of microbial origin (xanthan gum, scleroglucan gum), crosslinked homopolymers of acrylic acid or of acrylamidopropanesulfonic acid and associative polymers (polymers comprising hydrophilic regions and hydrophobic regions having a fatty chain (alkyl or alkenyl chain comprising at least 10 carbon atoms) that are capable, in an aqueous medium, of reversibly associating with one another or with other molecules).

According to one particular embodiment, the organic thickener is chosen from cellulose-based thickeners (hydroxyethyl cellulose, hydroxypropyl cellulose or carboxymethyl cellulose), guar gum and derivatives thereof (hydroxypropyl guar), gums of microbial origin (xanthan gum, scleroglucan gum) and crosslinked homopolymers of acrylic acid or of acrylamidopropanesulfonic acid, and preferably from cellulose-based thickeners in particular with hydroxyethyl cellulose.

The content of organic thickener(s), if they are present, usually ranges from 0.01% to 20% by weight and preferably from 0.1% to 5% by weight relative to the weight of the composition of the invention.

The composition of the invention generally comprises water and/or one or more organic solvents.

Examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols, for instance benzyl alcohol or phenoxyethanol, and mixtures thereof.

Such organic solvents may be present in proportions preferably of between 1% and 40% by weight and more preferentially between 5% and 30% by weight relative to the total weight of the composition.

Preferably, the composition of the invention comprises water. More preferably, the composition comprises at least 5% by weight of water, preferably at least 10% by weight of water and better still at least 20% by weight of water relative to its total weight.

The composition according to the present invention may also comprise one or more adjuvants, chosen from those conventionally used in compositions for dyeing keratin fibres, such as penetrants, sequestrants, fragrances, dispersants, film-forming agents, ceramides, preserving agents or opacifiers.

The above adjuvants may generally be present in an amount, for each of them, of between 0.01% and 20% by weight, relative to the weight of the composition.

The composition of the invention may result from the mixing of several compositions. More preferentially, it results from the mixing at the time of use (it is then referred to as a ready-to-use composition) of two or three compositions, even more preferentially of two compositions (A) and (B), (A) comprising one or more oxidation dyes as defined previously and (B) comprising one or more oxidizing agents as defined previously. Preferably, (A) comprises one or more basifying agents. The liquid fatty substance(s), the solid fatty alcohol(s), the oxyethylenated fatty alcohol(s) and the cationic polymer(s) of the invention are then, independently of each other, present in at least one of the compositions (A) or (B). Even more preferentially, the cationic polymer(s) are present only in composition (A).

Advantageously, composition (A) is in the form of an emulsion, a gel or a cream.

Advantageously, composition (B) is in the form of a solution, an emulsion or a gel.

A subject of the present invention is also a process for the oxidation dyeing of keratin fibres, comprising the application to the said wet or dry keratin fibres of the dye composition as described above.

According to the invention, this composition applied to the keratin fibres preferentially results from the mixing of compositions (A) and (B), this mixing being performed either before application to the keratin fibres (extemporaneous preparation) or directly on the keratin fibres (successive application to the fibres of compositions (A) and (B) without intermediate rinsing).

Thus, according to a first variant of the process according to the invention, compositions (A), and then (B), are applied to the wet or dry keratin fibres, successively and without intermediate rinsing.

According to a second variant of the process according to the invention, a composition obtained by extemporaneous mixing, before application, of the compositions (A) and (B) is applied to the wet or dry keratin fibres.

Independently of the variant used, the weight ratio of the amount of composition (A) used to the amount of composition (B) used may range from 0.2 to 3 and preferably from 0.5 to 2.

The pH of the final mixture applied to the hair may advantageously range from 6 to 11.5, better still from 7 to 11 and even better still from 8 to 11.

In addition, the composition of the invention, i.e. preferably the mixture present on the fibres (resulting either from the extemporaneous mixing of compositions (A) and (B) or from the successive application of these compositions) is left in place for a time generally from about 1 minute to 1 hour and preferably from 5 minutes to 30 minutes.

The temperature during the process is conventionally between room temperature (from 15 to 25° C.) and 80° C. and preferably between room temperature and 60° C.

After the treatment, the keratin fibres are generally rinsed with water, optionally washed with a shampoo and then rinsed with water, after which they are dried or left to dry.

Finally, a subject of the invention is also a multi-compartment dyeing device or "kit", comprising a first compartment containing a composition (A), and a second compartment containing a composition (B), compositions (A) and (B) being such that their mixing leads to the composition of the invention as described above.

This device may advantageously be equipped with a means for dispensing the desired mixture on the hair, such as the devices described in patent FR 2 586 913.

This device may be accompanied by one or more compositions for washing and/or conditioning keratin fibres, which are intended to be applied before or after the dyeing and/or bleaching treatment according to the invention.

The examples that follow serve to illustrate the invention without, however, being limiting in nature.

EXAMPLE

The oxidation dye compositions (A) below were prepared (in the table below, the amounts are expressed as grams of active material):

Dye Compositions (A):

| Compositions | A1 | A2 | A3 | A4 |
|---|---|---|---|---|
| Pentasodium pentetate | 0.8 | 0.8 | 0.8 | 0.8 |
| Thiolactic acid | — | 0.4 | 0.4 | — |
| Aqueous ammonia (expressed as $NH_3$) | 0.8 | 2.2 | — | 0.8 |
| Erythorbic acid | 0.3 | 0.3 | 0.3 | 0.3 |
| Sodium metabisulfite | 0.7 | — | — | 0.7 |
| Ethanolamine | 5.24 | 0.5 | 5.24 | 5.24 |
| Steareth-2 | 1.38 | 1.38 | 1.38 | 1.25 |
| Steareth-20 | 2.75 | 2.75 | 2.75 | 2.5 |
| 2,4-Diaminophenoxyethanol hydrochloride | 0.31 | — | — | — |
| N,N-Bis(2-hydroxyethyl)-p-phenylenediamine sulfate monohydrate | 0.28 | — | — | — |
| Resorcinol | 1.66 | 0.15 | — | 0.12 |
| m-Aminophenol | 0.14 | 0.009 | — | 0.0072 |
| p-Phenylenediamine | 2 | 0.137 | 0.35 | 0.1096 |
| 5-Amino-6-chloro-o-cresol | — | — | 0.21 | — |
| 4-Amino-2-hydroxytoluene | — | — | 0.98 | — |
| 2-Methylresorcinol | — | 0.013 | — | 0.0104 |
| 1-Hydroxyethyl-5-diaminopyrazole sulfate | — | — | 1.19 | — |
| Mineral oil | 8.8 | 8.8 | 8.8 | 8 |
| Cetylstearyl alcohol | 8.8 | 8.8 | 8.8 | 8 |
| *Camellia* oil | 0.2 | 0.2 | — | 0.2 |
| Olive oil | — | — | 0.2 | — |
| Hexadimethrine chloride (Mexomer PO from Chimex) | — | 0.3 | — | — |
| Polyquaternium-6 (Merquat 100 from Nalco) | 0.72 | 0.4 | 0.72 | 2 |
| Fragrance | 0.5 | 0.5 | 0.5 | 0.5 |
| Water | qs 100 | qs 100 | qs 100 | qs 100 |

Oxidizing Composition (B): (In Grams of Active Material)

| | |
|---|---|
| Hydrogen peroxide | 6 |
| Sodium stannate | 0.04 |
| Tetrasodium pyrophosphate decahydrate | 0.02 |
| Pentasodium pentetate | 0.06 |
| Glycerol | 0.5 |
| Cetylstearyl alcohol | 2.28 |
| Cetylstearyl alcohol containing 25 OE | 0.57 |
| Trideceth-2 carboxamide MEA | 0.85 |
| Water | qs 100 |

The compositions described above were mixed at the time of use in the following manner:
the dye composition (A1) was mixed with the oxidizing composition (B), in a weight ratio (A1):(B) of 1:1.5;
the dye composition (A2) was mixed with the oxidizing composition (B), in a weight ratio (A2):(B) of 1:1.5;
the dye composition (A3) was mixed with the oxidizing composition (B), in a weight ratio (A3):(B) of 1:1.5;
the dye composition (A4) was mixed with the oxidizing composition (B), in a weight ratio (A4):(B) of 1:1.

These mixtures led to ready-to-use compositions that are particularly easy to apply, and that remain localized at the point of application.

In each case, the mixture obtained was applied to locks of hair, at a rate of 10 g of mixture per 1 g of locks. After a leave-on time of 30 minutes, the locks were rinsed, washed with a standard shampoo and dried. The application is easy, the mixtures are easy to spread on the hair and remain localized on the locks.

In the four cases, the colorations obtained are very homogeneous and particularly strong.

The invention claimed is:
1. Composition for dyeing keratin fibres, comprising:
one or more oxidation dyes,
one or more basifying agents, one or more non-oxyalkylenated fatty substances that are liquid at room temperature, chosen from hydrocarbons containing more than 16 carbon atoms selected from the group consisting of liquid paraffins, liquid petroleum jelly, polydecenes, hydrogenated polyisobutene, squalane, and mixtures thereof,
one or more oxidizing agents,
one or more oxyethylenated fatty alcohols with a number of oxyethylene units of greater than or equal to 10,
one or more oxyethylenated fatty alcohols with a number of oxyethylene units of less than 10;
one or more non-oxyethylenated fatty alcohols that are solid at room temperature, and
one or more cationic polymers,
the content of one or more non-oxyalkylenated fatty substances that are liquid at room temperature ranging from 1% to 10% by weight relative to the total weight of the composition.

2. Composition according to claim 1, characterized in that the basifying agent is chosen from aqueous ammonia, alkaline carbonates, sodium hydroxide, potassium hydroxide, organic amines, and the compounds of formula (I) below:

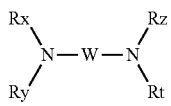
(I)

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom, or a $C_1$-$C_6$ alkyl, $C_1$-$C_6$ hydroxyalkyl, or $C_1$-$C_6$ aminoalkyl radical.

3. Composition according to claim 1, characterized in that the oxidizing agent is chosen from hydrogen peroxide, urea peroxide, alkali metal bromates or ferricyanides, peroxygenated salts, and redox enzymes optionally in the presence of the respective donor or cofactor thereof.

4. Composition according to claim 1, characterized in that the oxidation dyes are chosen from oxidation bases, optionally combined with one or more couplers.

5. Composition according to claim 1, characterized in that the oxyethylenated fatty alcohol(s) with a number of oxyethylene units of greater than or equal to 10 are chosen from those in which the number of oxyethylene units is greater than or equal to 15.

6. Composition according to claim 1, characterized in that the content of oxyethylenated fatty substances with a number of oxyethylene units of greater than or equal to 10 ranges from 0.1% to 10% by weight relative to the total weight of the composition.

7. Composition according to claim 1, characterized in that the oxyethylenated fatty alcohol(s) with a number of oxyethylene units of less than 10 are chosen from those in which the number of oxyethylene units is less than or equal to 5.

8. Composition according to claim 1, characterized in that the content of oxyethylenated fatty substances with a number of oxyethylene units of less than 10 ranges from 0.1% to 10% by weight relative to the total weight of the composition.

9. Composition according to claim 1, characterized in that the non-oxyethylenated fatty alcohol(s) that are solid at room temperature comprise from 14 to 30 carbon atoms.

10. Composition according to claim 1, characterized in that the content of non-oxyethylenated fatty alcohols that are solid at room temperature ranges from 0.1% to 20% by weight relative to the total weight of the composition.

11. Composition according to claim 1, characterized in that the cationic polymer(s) are chosen from:
(1) Homopolymers or copolymers derived from crosslinked or non-crosslinked acrylic or methacrylic esters or amides and comprising at least one of the units of formula (I), (II), (III) or (IV) below:

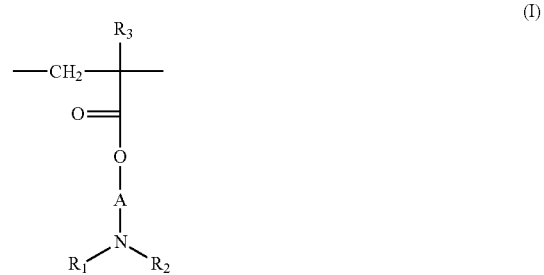
(I)

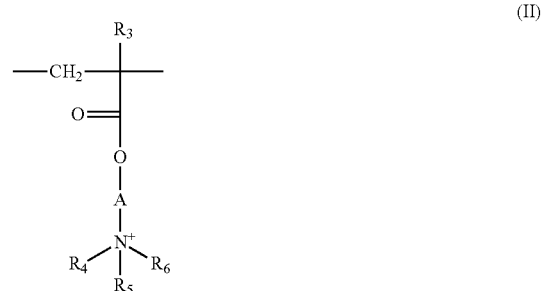
(II)

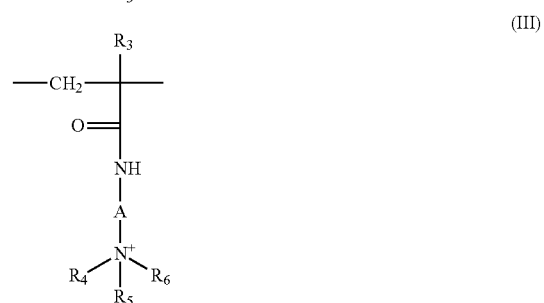
(III)

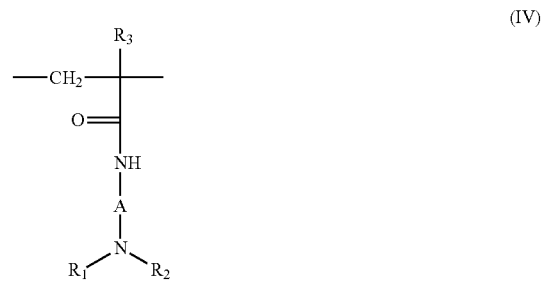
(IV)

in which:
$R_1$ and $R_2$, which are identical or different, each represent a hydrogen atom or an alkyl group having from 1 to 6 carbon atoms;
$R_3$, which may be identical or different at each occurrence, denotes a hydrogen atom or a $CH_3$ group;
A, which may be identical or different, in each case represents a linear or branched alkyl group of 1 to 6 carbon atoms, or a hydroxyalkyl group of 1 to 4 carbon atoms;

$R_4$, $R_5$ and $R_6$, which may be identical or different, each represent an alkyl group containing from 1 to 6 carbon atoms or a benzyl group;

$X^-$ denotes an anion derived from a mineral or organic acid or a halide;

(2) Cationic polysaccharides, especially those chosen from:

cellulose ether derivatives comprising quaternary ammonium groups;

cellulose copolymers or cellulose derivatives grafted with a water-soluble quaternary ammonium monomer;

guar gums containing trialkylammonium cationic groups;

(3) Polymers formed from piperazinyl units and divalent alkylene or hydroxyalkylene radicals containing straight or branched chains, optionally interrupted with oxygen, sulfur or nitrogen atoms or with aromatic or heterocyclic rings, and also the oxidation and/or quaternization products of these polymers;

(4) Water-soluble cationic polyaminoamides, prepared in particular by polycondensation of an acid compound with a polyamine; these polyaminoamides possibly being crosslinked with an epihalohydrin, a diepoxide, a saturated or unsaturated dianhydride, a bis-unsaturated derivative, a bis-halohydrin, a bis-azetidinium, a bis-haloacyldiamine or a bis-alkyl halide or else by an oligomer resulting from the reaction of a bifunctional compound which is reactive towards a bis-halohydrin, a bis-azetidinium, a bis-haloacyldiamine, a bis-alkyl halide, an epihalohydrin, a diepoxide or a bis-unsaturated derivative; these polyaminoamides possibly being alkylated, or quaternized if they contain one or more tertiary amine functions;

(5) Polyamino amide derivatives resulting from the condensation of polyalkylene polyamines with polycarboxylic acids followed by alkylation with difunctional agents;

(6) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 6 carbon atoms;

(7) Alkyldiallylamine or dialkyldiallylammonium cyclopolymers comprising, as the main constituent of the chain, units corresponding to the formula (V) or (VI):

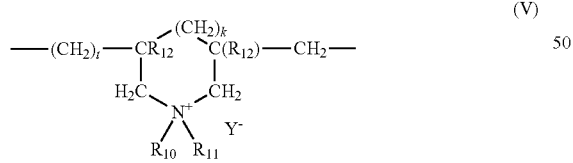

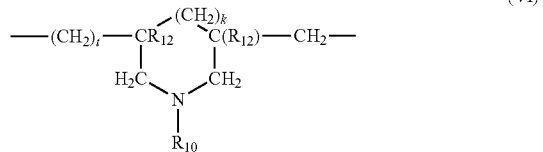

in which k and t are equal to 0 or 1, the sum k+t being equal to 1; $R_{12}$ denotes a hydrogen atom or a methyl group; $R_{10}$ and $R_{11}$, independently of one another, denote an alkyl group having from 1 to 6 carbon atoms, a hydroxyalkyl group in which the alkyl group has 1 to 5 carbon atoms, a lower amidoalkyl group (i.e. the alkyl part of which is $C_1$-$C_4$), or else $R_{10}$ and $R_{11}$ may, together with the nitrogen atom to which they are attached, denote heterocyclic groups; $Y^-$ is an anion;

(8) The quaternary diammonium polymers containing repeating units corresponding to formula (VII):

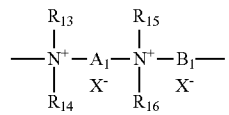

in which:

$R_{13}$, $R_{14}$, $R_{15}$ and $R_{16}$, which may be identical or different, represent aliphatic, alicyclic or arylaliphatic groups containing from 1 to 6 carbon atoms or lower hydroxyalkylaliphatic groups (i.e. the alkyl part of which is $C_1$-$C_4$), or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ each represent a linear or branched $C_1$-$C_6$ alkyl group substituted with a nitrile, ester, acyl or amide group or a —CO—O—$R_{17}$-E or —CO—NH—$R_{17}$-E group where $R_{17}$ is an alkylene group and E is a quaternary ammonium group;

$A_1$ and $B_1$ represent polymethylene groups containing from 2 to 8 carbon atoms, which may be linear or branched and saturated or unsaturated and may contain, joined to or intercalated in the main chain, one or more aromatic rings, or one or more oxygen or sulfur atoms or sulfoxide, sulfone, disulfide, amino, alkylamino, hydroxyl, quaternary ammonium, ureido, amide or ester groups; and $X^-$ denotes an anion derived from a mineral or organic acid;

$A_1$, $R_{13}$ and $R_{15}$ may, with the two nitrogen atoms to which they are attached, form a piperazine ring; moreover, if $A_1$ denotes a linear or branched, saturated or unsaturated alkylene or hydroxyalkylene group, $B_1$ may also denote a group:

—$(CH_2)_n$—CO-E'-OC—$(CH_2)_n$— in which n denotes an integer from 0 to 7 and E' denotes:

a) a glycol residue of formula —O—Z—O—, in which Z denotes a linear or branched hydrocarbon-based group, or a group corresponding to one of the following formulae:

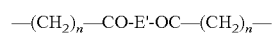

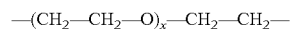

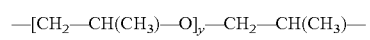

in which x and y each denote an integer from 1 to 4, representing a defined and unique degree of polymerization or any number from 1 to 4 representing an average degree of polymerization;

b) a bis-secondary diamine residue;

c) a bis-primary diamine residue of formula —NH—Y—NH—, in which Y denotes a linear or branched hydrocarbon-based group, or alternatively the divalent group —$CH_2$—$CH_2$—S—S—$CH_2$—$CH_2$—;

d) a ureylene group of formula —NH—CO—NH—.

(9) Polyquaternary ammonium polymers consisting of units of formula (IX):

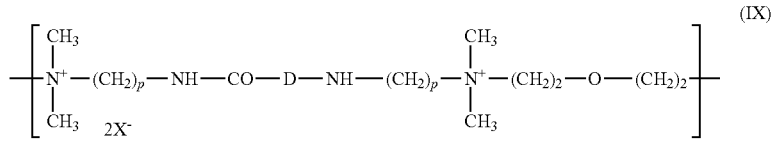 (IX)

in which:

p denotes an integer ranging from 1 to 6 approximately;

D may be nothing or may represent a group —$(CH_2)_r$—CO— in which r denotes a number equal to 4 or 7; and $X^-$ denotes an anion derived from a mineral or organic acid;

(10) Quaternary polymers of vinylpyrrolidone and of vinylimidazole;

(11) Ethoxylated cationic tallow polyamines;

(12) Vinylamide homopolymers or copolymers;

(13) Cationic polyurethanes;

(14) Cationic proteins or cationic protein hydrolysates, polyalkyleneimines, polymers containing vinylpyridine or vinylpyridinium units, and chitin derivatives.

12. Composition according to claim 1, characterized in that the content of cationic polymers ranges from 0.01% to 10% by weight relative to the weight of the composition.

13. Composition according to claim 1, characterized in that it results from the mixing of several compositions.

14. Process for dyeing keratin fibres, comprising the application to the said wet or dry fibres of the dye composition as defined according to claim 1.

15. Process for dyeing keratin fibres according to claim 14, comprising the application of compositions (A) and then (B), successively and without intermediate rinsing, to the said wet or dry fibres, (A) comprising one or more oxidation dyes and (B) comprising one or more oxidizing agents.

16. Process for dyeing keratin fibres according to claim 14, comprising the application to the said wet or dry fibres of a composition obtained by the extemporaneous mixing of compositions (A) and then (B), (A) comprising one or more oxidation dyes and (B) comprising one or more oxidizing agents.

17. Multi-compartment dyeing device or "kit", comprising a first compartment containing a composition (A), and a second compartment containing a composition (B), compositions (A) and (B) being such that their mixing leads to a composition as defined in claim 1.

* * * * *

UNITED STATES PATENT AND TRADEMARK OFFICE
CERTIFICATE OF CORRECTION

PATENT NO. : 9,849,071 B2
APPLICATION NO. : 14/367042
DATED : December 26, 2017
INVENTOR(S) : G. Fack et al.

Page 1 of 1

It is certified that error appears in the above-identified patent and that said Letters Patent is hereby corrected as shown below:

In the Claims

| Column | Line | ERROR |
|---|---|---|
| 33 (Claim 11, Lines 80-81) | 18 | "and also the oxidation and/or quaternization products of these polymers;" should read --and the oxidation and/or quaternization products of these polymers;-- |
| 33 (Claim 11, Line 88) | 25 | "halide or else by an" should read --halide or by an-- |
| 34 (Claim 11, Line 128) | 2 | "or else $R_{10}$ and $R_{11}$" should read --or $R_{10}$ and $R_{11}$-- |

Signed and Sealed this
Twenty-second Day of October, 2019

Andrei Iancu
*Director of the United States Patent and Trademark Office*